(12) United States Patent
Lazarev et al.

(10) Patent No.: US 8,231,070 B2
(45) Date of Patent: Jul. 31, 2012

(54) DEVICES, METHODS AND APPLICATIONS FOR EXTRACTION OF MOLECULES FROM POLYMERIC GEL ELECTROPHORETIC MEDIA

(75) Inventors: Alexander Lazarev, Lexington, MA (US); Thomas Rejtar, Somerville, MA (US); Barry L. Karger, Newton, MA (US)

(73) Assignee: Northeastern University, Boston, MA (US)

( * ) Notice: Subject to any disclaimer, the term of this patent is extended or adjusted under 35 U.S.C. 154(b) by 517 days.

(21) Appl. No.: 12/302,414

(22) PCT Filed: May 29, 2007

(86) PCT No.: PCT/US2007/012729
§ 371 (c)(1),
(2), (4) Date: Nov. 25, 2008

(87) PCT Pub. No.: WO2007/140016
PCT Pub. Date: Dec. 6, 2007

(65) Prior Publication Data
US 2009/0188999 A1    Jul. 30, 2009

Related U.S. Application Data

(60) Provisional application No. 60/808,926, filed on May 26, 2006.

(51) Int. Cl.
*B02C 19/00* (2006.01)
(52) U.S. Cl. ............ 241/1; 241/2; 241/19; 241/20; 241/301
(58) Field of Classification Search ............ 241/1, 2, 241/301, 19, 20
See application file for complete search history.

(56) References Cited

U.S. PATENT DOCUMENTS

| 3,072,362 | A |   | 1/1963 | Allen |   |
|---|---|---|---|---|---|
| 3,493,503 | A | * | 2/1970 | Mass | 210/778 |
| 3,802,843 | A | * | 4/1974 | Kim | 422/71 |
| 3,941,317 | A | * | 3/1976 | Kanor | 241/21 |

(Continued)

OTHER PUBLICATIONS

Bergen, H.R., et al.; "Normalization of relative peptide ratios derived from in-gel digests: applications to protein variant analysis at the peptide level"; Rapid Commun. Mass. Spectrom.; (2005); 19: 2871-2877.

(Continued)

*Primary Examiner* — Bena Miller
(74) *Attorney, Agent, or Firm* — Weingarten, Schurgin, Gagnebin & Lebovici LLP

(57) ABSTRACT

A device and method to provide a simplified wash process and controlled disintegration of a soft substance, such as a gel, are disclosed. In use, a block of, e.g., gel matrix is placed in the device and washed with a series of appropriate solutions to remove interfering contaminants. The washing liquid is removed through a deformable narrow opening in the bottom of the device, and, subsequently, the gel block is extruded through the deformable narrow opening, by a physical force, such as centrifugal force, a vacuum or positive pressure from a gas or liquid, etc., resulting in fragmentation of the gel block into a series of particles of similar size. The fragmentation of the gel results from shear forces exerted onto the gel block traveling through the deformable narrow opening in the device. The rate of such fragmentation and resulting fragment size can be controlled by extruding the gel block using a predefined level of force as well as by controlling the dimensions and shape of the narrow opening (s) in the device.

15 Claims, 12 Drawing Sheets

U.S. PATENT DOCUMENTS

| | | | |
|---|---|---|---|
| 4,350,768 A | | 9/1982 | Tihon et al. |
| 5,127,895 A | * | 7/1992 | Pawlovich ............... 494/16 |
| 5,171,138 A | * | 12/1992 | Forrest .................... 418/48 |
| 5,624,295 A | * | 4/1997 | Watkins .................. 446/475 |
| 5,823,850 A | * | 10/1998 | Watkins .................. 446/475 |
| 6,209,439 B1 | | 4/2001 | Repac et al. |
| 6,336,796 B1 | * | 1/2002 | Cholet et al. ............. 418/48 |
| 6,358,474 B1 | * | 3/2002 | Dobler et al. ............ 422/535 |
| 6,916,423 B2 | * | 7/2005 | Bogoev et al. ........... 210/634 |
| 7,270,284 B2 | | 9/2007 | Liao et al. |
| 2003/0203800 A1 | * | 10/2003 | Aizawa et al. ............ 494/16 |
| 2005/0089144 A1 | * | 4/2005 | Fukushima et al. ...... 378/144 |

OTHER PUBLICATIONS

Bunai, K., et al.; "Proteomic analysis of acrylamide gel separated proteins immobilized on polyvinylidene difluoride membranes following proteolytic digestion in the presence of 80% acetonitrile"; Proteomics; (2003); 3: 1738-1749.

Castellanos-Serra, L., et al.; "An in-gel digestion procedure that facilitates the identification of highly hydrophobic proteins by electrospray ionization-mass spectrometry analysis"; Proteomics; (2005); 5: 2729-2738.

De Godoy, L., et al.; "Status of complete proteome analysis by mass spectrometry: SILAC labeled yeast as a model system"; Genome Biology; (2006); 7(6): R50.1-R50.15.

Finehout, E.J. and Lee, K.H.; "Comparison of automated in-gel digest methods for femtomole level samples"; Electrophoresis; (2003); 24: 3508-3516.

Havlis, J., et al.; "Fast-Response Proteomics by Accelerated In-Gel Digestion of Proteins"; Anal. Chem.; (2003); 75: 1300-1306.

Havlis, J. and Schevchenko, A.; "Absolute Quantification of Proteins in Solutions and in Polyacrylamide Gels by Mass Spectrometry"; Anal. Chem.; (2004); 76: 3029-3036.

Katayama, H., et al.; "Optimization of in-gel protein digestion system in combination with thin-gel separation and negative staining in 96-well plate format"; Rapid Commun. Mass. Spectrom.; (2003); 17: 1071-1078.

Katayama, H., et al.; "Efficient in-gel digestion procedure using 5-cyclohexyl-1-pentyl-beta-D-maltoside as an additive for gel-based membrane proteomics"; Rapid Commun. Mass. Spectrom; (2004); 18: 2388-2394.

Kumarathasan, P., et al.; "An optimized protein in-gel digest method for reliable proteome characterization by MALDI-TOF-MS analysis"; Anal. Biochem.; (2005); 346: 85-89.

Lopez-Ferrer, D., et al.; "Ultra Fast Trypsin Digestion of Proteins by High Intensity Focused Ultrasound"; J. Proteome Res.; (2005); 4(5): 1569-1574.

Lu, X and Zhu, H.; "Tube-Gel Digestion: A Novel Proteomic Approach for High Throughput Analysis of Membrane Proteins"; Mol. Cell Proteomics; (2005); 4(12): 1948-1958.

Nomura, E., et al.; "Acid-labile surfactant improves in-sodium dodecyl sulfate polyacrylamide gel protein digestion for matrix-assisted laser desorption/ionization mass spectrometric peptide mapping"; J. Mass. Spectrom.; (2004); 39: 202-207.

Ong, S.E., et al.; "Poster A050496—Comparing in-solution and in-gel enzymatic digestion efficiencies using SILAC"; Proceedings of the $53^{rd}$ ASMS Conference on Mass. Spectrometry, San Antonio, Texas (2005).

Russell, W.K., et al.; "Proteolysis in Mixed Organic-Aqueous Solvent Systems: Applications for Peptide Mass Mapping Using Mass Spectrometry"; Anal. Chem.; (2001); 73: 2682-2685.

Speicher, K.D., et al.; "Systematic Analysis of Peptide Recoveries from In-Gel Digestions for Protein Identifications in Proteome Studies"; Journal of Biomolecular Techniques; (2006); 11: 74-86.

Strader, M.B., et al.; "Efficient and Specific Trypsin Digestion of Microgram to Nanogram Quantities of Proteins in Organic-Aqueous Solvent Systems"; Anal. Chem; (2006); 78: 125-134.

Sun, W., et al.; "Microwave-assisted Protein Preparation and Enzymatic Digestion in Proteomics"; Mol. Cell Proteomics; (2006); 5: 769-776.

Terry, D.E., et al.; "Optimized Sample-Processing Time and Peptide Recovery for the Mass Spectrometric Analysis of Protein Digests"; J. Am. Soc. Mass. Spectrom.; (2004); 15: 784-794.

Yokono, T., et al.; "Improvement of Automatic In-Gel Digestion by in Situ Alkylation of Proteins"; J. Biomol. Tech.; (2003); 14(3): 191-196.

* cited by examiner

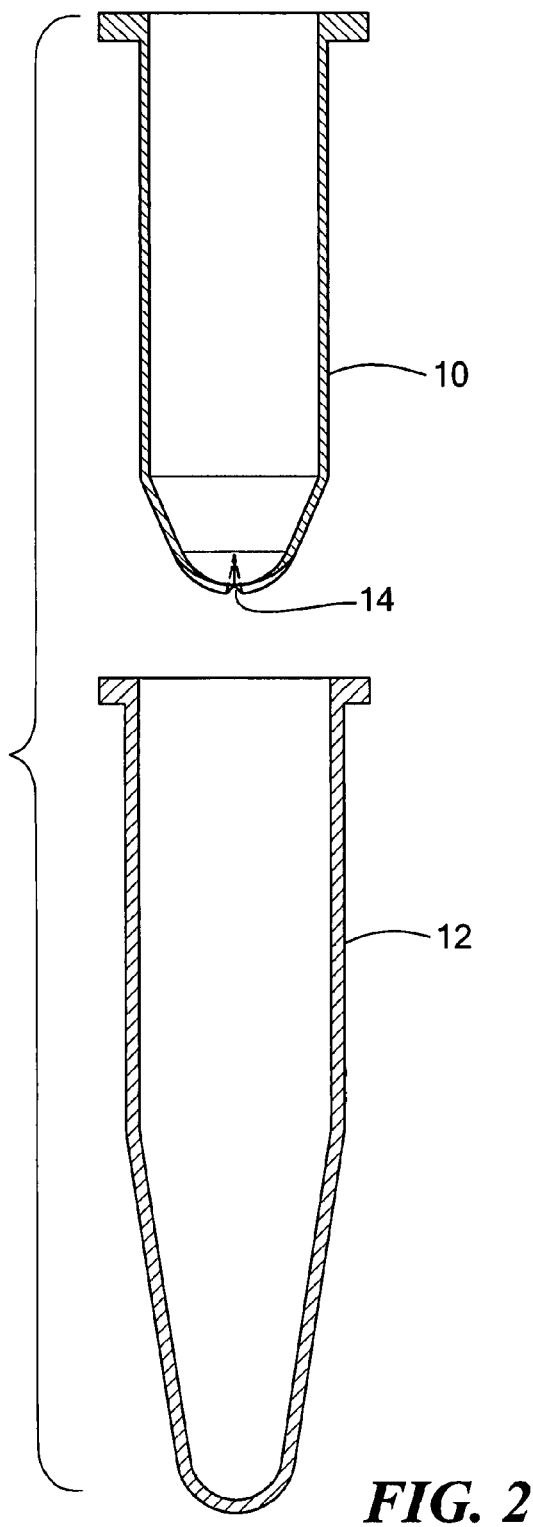
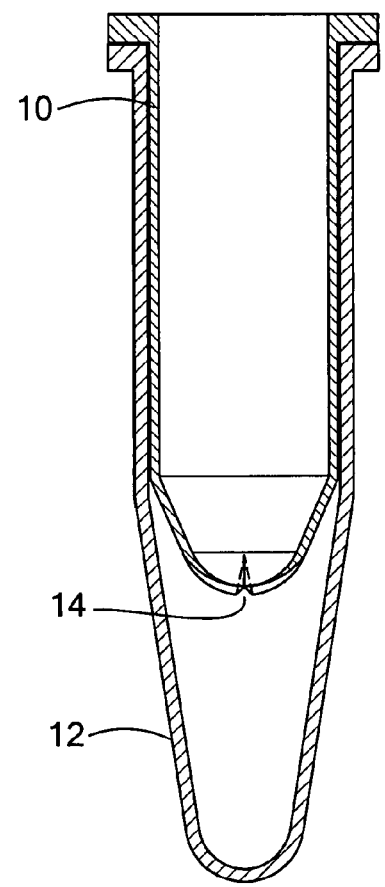
*FIG. 2*
*FIG. 3*

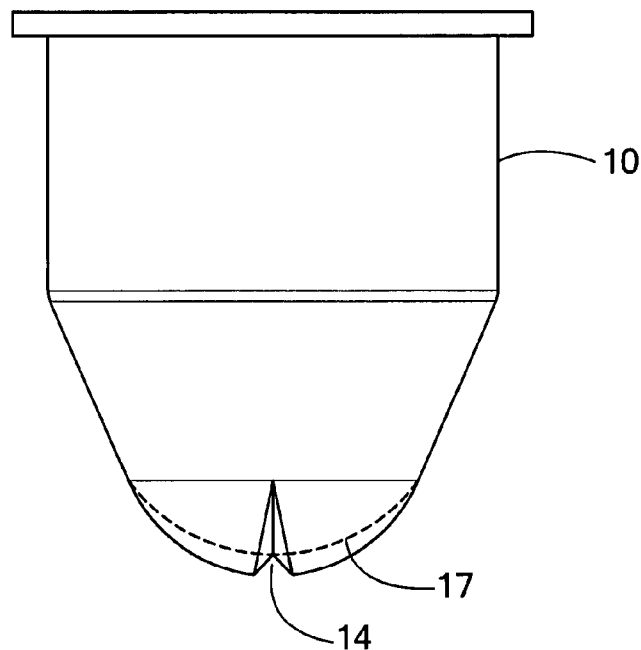
FIG. 5a
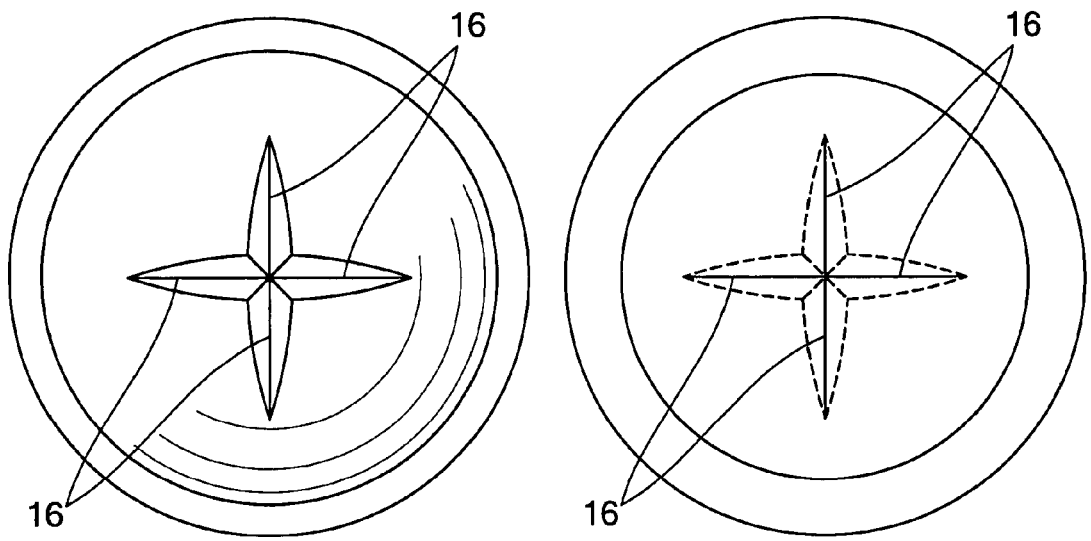
FIG. 5b  FIG. 5c

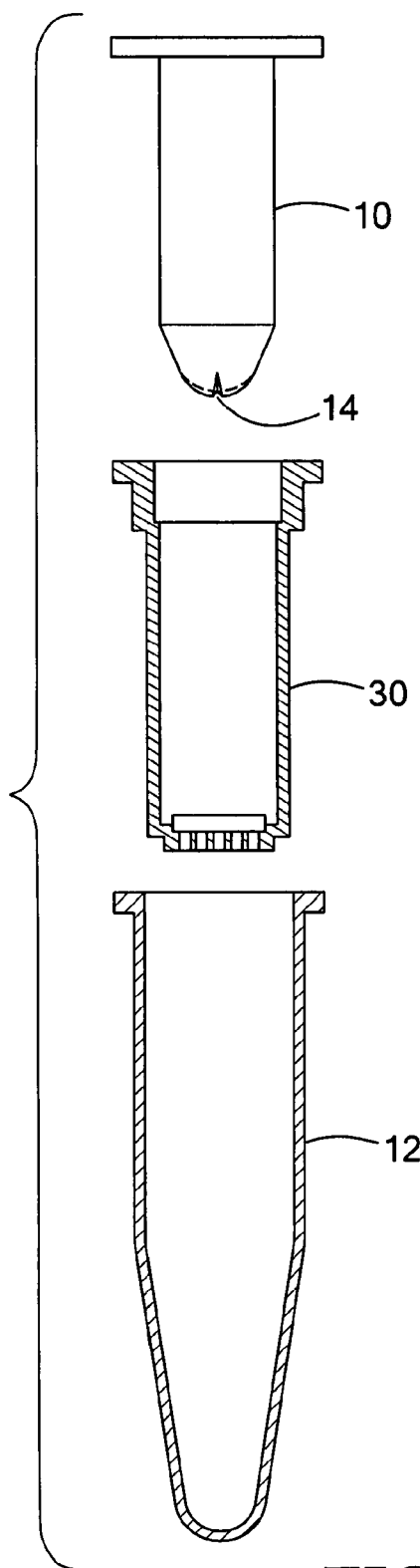
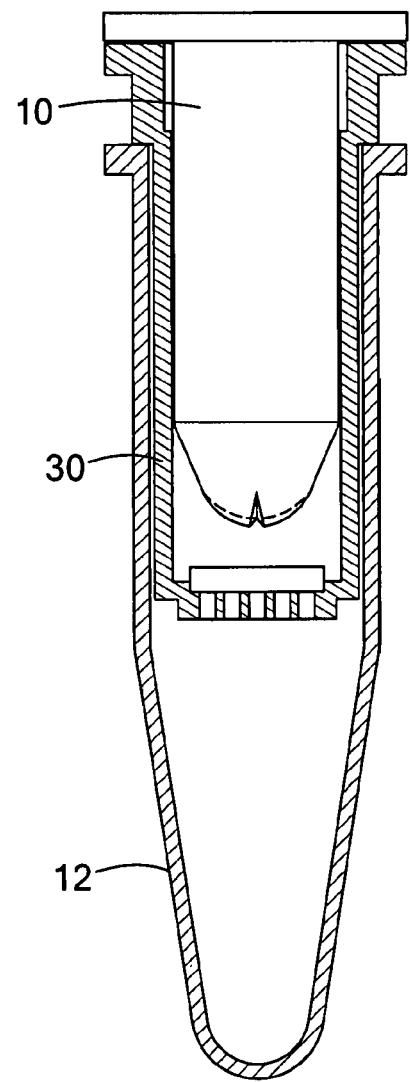
FIG. 9a
FIG. 9b

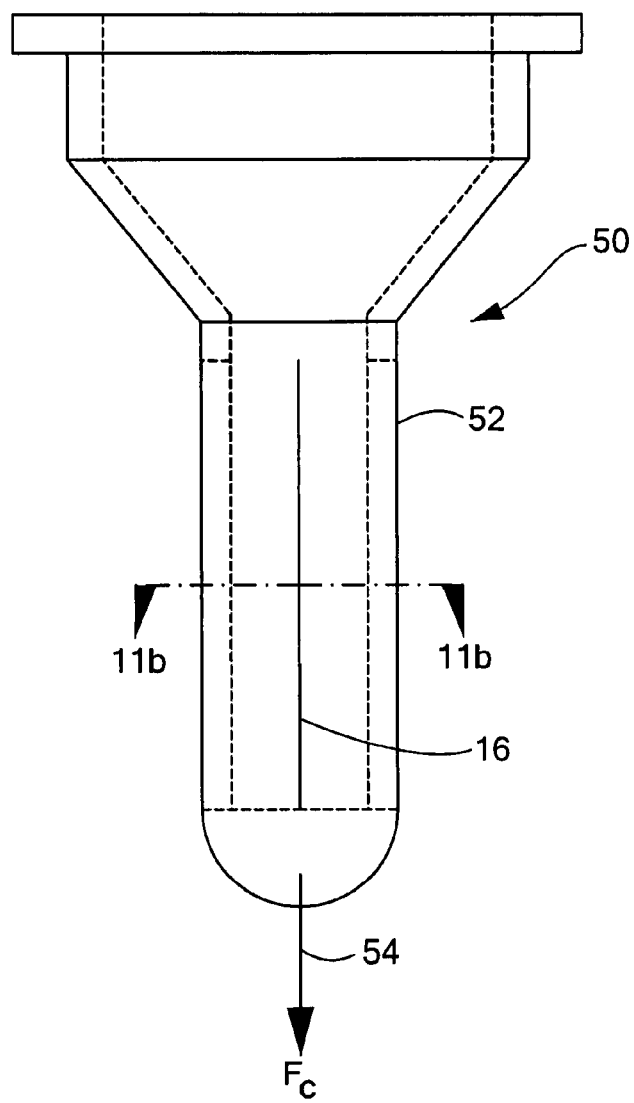
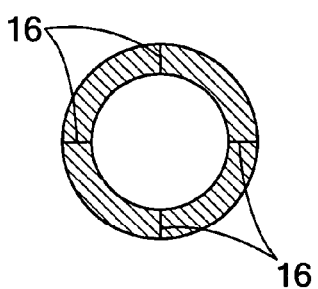
*FIG. 11b*
*FIG. 11a*

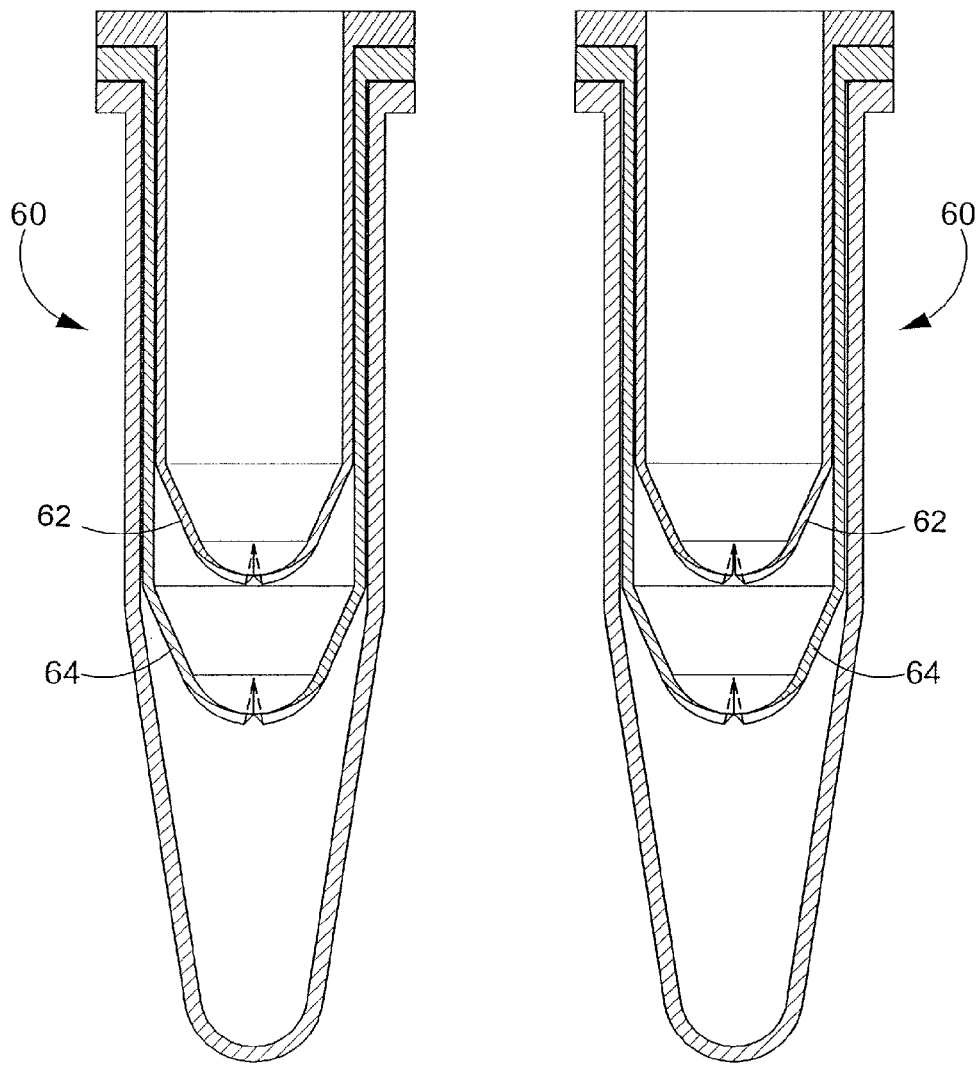
*FIG. 13*  *FIG. 14*

DEVICES, METHODS AND APPLICATIONS FOR EXTRACTION OF MOLECULES FROM POLYMERIC GEL ELECTROPHORETIC MEDIA

CROSS REFERENCE TO RELATED APPLICATIONS

This application claims the priority of U.S. Provisional Application No. 60/808,926, filed May 26, 2006, entitled DEVICES, METHODS AND APPLICATIONS FOR EXTRACTIONS OF MOLECULES FROM POLYMERIC GEL ELECTROPHORETIC MEDIA, the whole of which is hereby incorporated by reference herein.

STATEMENT REGARDING FEDERALLY SPONSORED RESEARCH OR DEVELOPMENT

N/A

BACKGROUND OF THE INVENTION

Separation of proteins on polyacrylamide gels is one of the most popular methods used in proteomics and biochemistry research today. While considerable attention is being paid in recent years to the development of automated multi-dimensional chromatographic techniques for protein identification, a predominant amount of proteomic work is still performed using polyacrylamide gel separations. Introduction of the pre-cast two-dimensional gels and immobilized pH gradient media have considerably simplified the art of 2D protein separation. Methods based on various combinations of chromatography and one-dimensional gel separations are also becoming popular, particularly capitalizing on the fact that SDS-PAGE separation (sodium dodecyl sulfate polyacrylamide gel electrophoresis) is, perhaps, the most efficient way to remove protein-bound detergents. Chromatographic alternatives are yet to match convenience and high resolution with respect to protein separation, offered by polyacrylamide gels in two-dimensional format as well as in a single dimension, either isoelectric focusing (IEF) or one-dimensional SDS-PAGE.

With the wide availability of high-end mass spectrometry instrumentation and growing popularity of stable isotope labeling techniques, it has become apparent that conventional in-gel digestion procedures suffer from incomplete digestion of proteins and problems related to the recovery of certain peptides out of the gel (Havliš et al., 2004). Previous reports describe many attempts to analyze the nature of the losses and eliminate some of their causes by using optimization of the methods (Terry et al., 2004; Kumarathasan et al., 2005; Castellanos-Serra et al., 2005; Bergen et al., 2005; Finehout et al., 2003; Yokono et al., 2003; Katayama et al., 2003; Lu et al., 2005), detergents (Nomura et al., 2004; Katayama et al., 2003), organic solvents (Russell et al., 2001; Havliš et al. 2003; Bunai et al., 2003; Strader et al., 2006), microwave radiation (Lopez-Ferrer et al., 2005) or ultrasound (Sun et al., 2006). However, the underlying problems still remain partially unsolved, as illustrated by one-dimensional gel electrophoresis followed by electrospray tandem mass spectrometry (GeLCMS) and SILAC isotopic labeling techniques (de Godoy et al., 2006).

During the separation in polyacrylamide gel, either in SDS-PAGE or in a second dimension of a 2D electrophoresis method, proteins coated by charged SDS molecules are driven through the pores of the polyacrylamide gel matrix by considerable forces in the electric field. Once the electric field is turned off and SDS is removed by gel fixation, proteins are thought to remain in the gel matrix during staining, imaging, spot excision, washes and de-staining. However, it is also assumed that another protein molecule, such as trypsin (ca. 24 kDa protein) or larger proteolytic enzymes, penetrate the gel matrix with no restriction during rehydration of gel plugs during the in-gel digestion step. In fact, proteases do enter the gel. However, it is expected that their concentration in the region of the highest substrate concentration, in the middle of the gel plug, would be considerably smaller than on the gel plug periphery, as a gel filtration phenomenon should take place and restrict protease entry into the gel matrix during gel plug rehydration. This phenomenon typically results in limited access of the enzyme to its substrate during proteolytic in-gel digestion, leading to diminishing peptide recovery and the occurrence of random missed cleavages. Similarly, extraction of certain products of proteolytic cleavage, particularly large hydrophobic peptides, is also restricted by the gel matrix. Furthermore, many traditional manual protocols and their robotic implementations call for organic solvent extraction steps. If the gel plugs are large enough, addition of 50% acetonitrile dehydrates the gel, beginning from the surface of the gel plug, sufficiently shrinking the acrylamide lattice to restrict peptide diffusion through it. Application of mild detergents during in-gel digestion steps has been shown to mitigate this problem to some extent by keeping the proteins and peptides in a more soluble state (Katayama et al., 2004). Nevertheless, mechanical obstruction for enzyme penetration into the gel and for peptide extraction out of it still presents a problem.

A common trend, employed by many groups to minimize this problem, is a manual cutting of the gel bands with the razor blade into cubes approximately 1 $mm^3$ in size to improve enzymatic digestion and peptide recovery from the polyacrylamide gel matrix. However, the elevated risk of protein loss by diffusion from smaller gel pieces during washing and de-staining steps can preclude the use of this technique immediately after gel excision, while manual cutting of gel plugs after they have been washed and de-stained inevitably can lead to errors due to loss of gel plugs, which are practically invisible in their rehydrated state.

A wide variety of robotic gel processors is offered by several manufacturers. However, commercial robotic in-gel digestion systems often exceed the throughput requirements of many laboratories, frequently forcing a user to work in a 96-well format, regardless of the number of samples being processed. The growing popularity of Gel-LC-MS workflow reduces throughput requirements even further, while many large robotic systems are not optimized to handle large segments of SDS-PAGE gels containing several protein bands.

BRIEF SUMMARY OF THE INVENTION

The invention is directed to a device and method for washing and/or shredding a material under an applied external force. A device according to the invention includes a substantially cylindrical body extending from an upper end to a lower end; a fixed opening at the upper end of the device body; and a deformable opening area disposed at the lower end of the device body and having an opening deformable at least sufficiently for the passage of liquid under an externally applied force greater than ambient pressure, said force comprising centrifugal force or positive or negative pressure from a gas or liquid, said lower end opening remaining closed to the passage of liquid under ambient pressure. Preferably, the device includes a cylindrical body extending from an upper end to a lower end, the cylindrical body defining a longitudinal axis from the upper end to the lower end, the cylindrical body having an inner surface and an outer surface; a fixed opening at the upper end of the cylindrical body; a mounting fitting on the cylindrical body adjacent the upper end for mounting the cylindrical body coaxially within a centrifuge tube; and a deformable opening area formed of a deformable material disposed at the lower end of the cylindrical body, wherein the deformable opening area has a thickness extending between an inner surface and an outer surface, the inner surface of the deformable opening area being contiguous with the inner surface of the cylindrical body, and the outer surface of the deformable opening area being contiguous with the outer surface of the cylindrical body, said deformable opening area comprising an opening deformable at least sufficiently for the passage of liquid under an externally applied force greater than ambient pressure, said force comprising centrifugal force or positive or negative pressure from a gas or liquid, said deformable opening area opening remaining closed to the passage of liquid under ambient pressure. Most preferably, the opening in said deformable opening area comprises three or more (preferably four) slots formed therein, said slots meeting at and extending radially from a common point, wherein each slot comprises two walls each extending through the thickness of the deformable opening area; the walls of each slot are disposed at an angle to each other such that the walls are closest to each other at the inner surface of the deformable opening area and are farthest from each other at the outer surface of the deformable opening area; the walls of each slot intersect the inner surface of the deformable opening area to form a cutting edge; and the walls of each slot are deformable to widen at the inner surface of the deformable opening area. Alternatively, the opening in said deformable opening area comprises a spiral slot formed therein, said spiral decreasing from the outer region of said deformable opening area to the center region of said deformable opening area. Preferred materials of the deformable opening area are an elastomeric material, e.g., a polymer, especially a thermoplastic polymer. Exemplary materials for the deformable opening area include polypropylene, polytetrafluoroethylene, polyethylene, polycarbonate, polysulphone or ABS. In one embodiment, the mounting fitting comprises an annular shoulder at the upper end of the cylindrical body extending radially outwardly with respect to the longitudinal axis of the cylindrical body. Systems according to the invention include a device according to the invention in combination with, e.g., a collection device, wherein said collection device has a substantially cylindrical body having an open top and a closed bottom and wherein the device according to the invention is sized to fit snugly into said collection device, through the open top thereof. Multiple additional devices according to the invention can be included in such systems, e.g., nested in series or configured in parallel, e.g., in a multi-well format.

The system and method according to the invention provide solutions for moderate throughput in-gel digestion applications and are also suitable for processing larger segments of gels, e.g., SDS-PAGE. Use of the system according to the invention advantageously minimizes manual handling of gel plugs or bands throughout the execution of an entire in-gel digestion protocol, following the gel plug excision through peptide extraction. The systems of the invention are particularly appropriate for robotic implementation. For example, these devices allow integrated washing, de-staining and shredding of gel bands into uniform blocks of controlled size, approximately 100-300 µm, prior to the enzymatic digestion and extraction of peptides. Such treatment increases the surface area of gel pieces and promotes improved gel re-hydration which allows the enzymes and solvent to better penetrate the gel lattice. The method according to the invention substantially cuts time spent on tedious manual handling of gel bands and minimizes the risk of sample contamination. In addition, this method improves the efficiency of enzymatic digestion and/or extraction steps.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings, in which:

FIG. 2 is a section through the device and receiving tube of FIG. 1;

FIG. 3 is a section through a nested shredding device and receiving tube;

FIG. 5a is a side elevation of another (more blunt) embodiment of a shredding device according to the invention;

FIGS. 5b and 5c are outside bottom and inside bottom schematic views, respectively, of the embodiment of FIG. 5a;

FIGS. 8-14 are alternative embodiments of the device of FIG. 1.

DETAILED DESCRIPTION OF THE INVENTION

Figure 1:
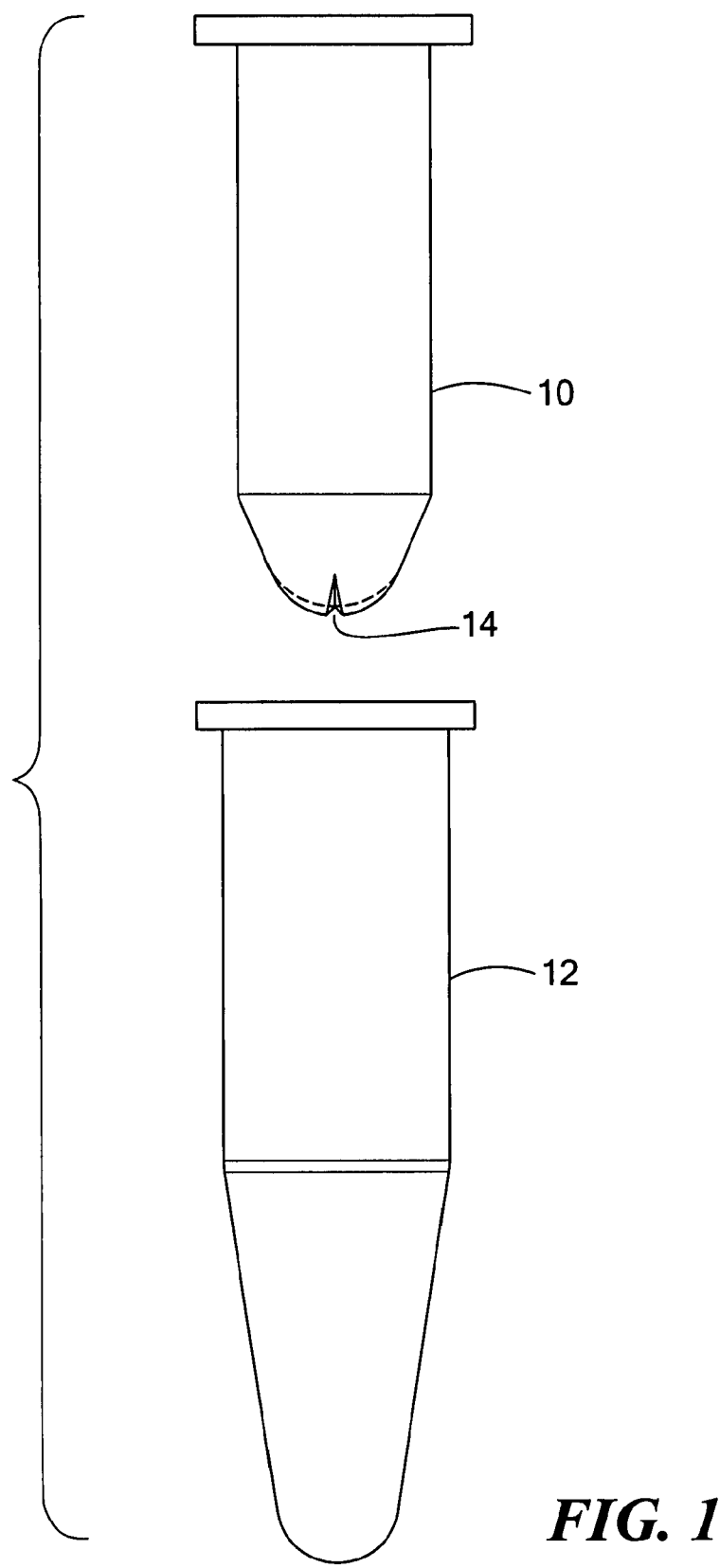
FIG. 1 is a side, exploded view of a shredding device according to the invention and an accompanying receiving tube to capture washing fluid or shredded material.

The invention is directed to a device and method for its use to provide a simplified wash process and controlled disintegration of a soft substance, such as a gel. In use, a block of, e.g., gel matrix is placed in the device and washed with a series of appropriate solutions to remove interfering contaminants. The washing liquid is removed through a deformable narrow opening in the bottom of the device, and, subsequently, the gel block is extruded through the deformable narrow opening, by a physical force, such as centrifugal force, a vacuum or positive pressure from a gas or liquid, etc., resulting in fragmentation of the gel block into a series of particles of similar size. The fragmentation of the gel results from shear forces exerted onto the gel block traveling through the deformable narrow opening in the device. The rate of such fragmentation and resulting fragment size can be controlled by extruding the gel block using a predefined level of force as well as by controlling the dimensions and shape of the narrow opening(s) in the device.

The shredding device according to the invention is designed to contain particles of gel and any solution (e.g., washing solution) at ambient pressure in the absence of an applied external force, such as a centrifugal force, and to open up as a function of the applied, e.g., centrifugal, force and to pass solutions through the deformable narrow opening at a relatively low centrifugal force (higher than 0 and lower than 3000 RCF (g)). The shredding device provides the means for mechanical disintegration of, e.g., solid or gel pieces into smaller particles upon application of a higher centrifugal force (ranging from 1000 RCF to 18,000 RCF) by passing the solid or gel material through the deformable narrow opening, e.g., a single slot or a series of slots, hole or a series of holes (other shape opening or multiple openings are possible) in the bottom of the device.

The initial size of the slots (in the absence of an applied force) is less then 100 µm; a preferred size is 1-5 µm to allow the surface tension of the solution to keep any solution from passing through the slots. Alternatively, the gaps in the slot openings can be filled with a thin layer of polymer material, which breaks at a predefined, e.g., centrifugal force. Upon application of the predefined centrifugal force (higher than 0 and lower than 3000 RCF), the slot dimensions increase due to the action of the centrifugal force on the segments/sectors comprising the bottom of the device.

Exemplary device volumes range from 10 µl to 5000 µl. A shredding device from 8.6 to 8.85 mm in diameter with a wider shoulder on top will fit inside and remain suspended on the top of a standard 1.5 ml Eppendorf-style centrifuge tube, as a collection or receiving tube, during centrifugation. Alternatively, a device 6.0 to 6.4 mm in diameter and with the wider shoulder on top will fit inside the standard 700 µl Eppendorf-style centrifuge tube. In another embodiment, a 14.5 to 14.8 mm diameter device with a wider shoulder on top will fit inside the standard 15 ml BD Falcon-style centrifuge tube, and a 24.8 to 25.2 mm diameter device with a wider shoulder or threaded cap on top will fit inside the standard 40 ml Sarstedt-style centrifuge tube.

In yet another embodiment, a single device can comprise two or more shredding elements, which are used concurrently. For example, a 96-well shredder device allows processing of any number of samples between 1 and 96 in parallel using commercially available microtiter plate centrifuge rotors or adapters. The shredding surfaces are introduced at the bottom of each of the 96 wells arranged in a microtiter plate format compatible with SBS standardized microplate dimensions. In another embodiment, a shredder device may be used in combination with a commercially available microfilter, such as Amicon UltraFree MC. Such a configuration allows the capture of the shredded particles on a microporous or ultrafiltration membrane filter and permits them to be treated with enzymatic or chemical reagents on the same filter. When the reaction is completed, a second centrifugation step drives the reactants through the filter, into the receiving container.

In yet another embodiment, a single device can comprise two or more shredding elements used consecutively, where the second shredding element is positioned directly below the first one, and the next shredding element below that one, and each subsequent shredding element is constructed from a less flexible material than the previous one. Such a configuration allows shredding of the sample material (gel) first to medium-size blocks at medium centrifugal force to facilitate more complete washing and removal of dyes and detergents. Subsequently, the medium-size gel blocks are processed at the higher centrifugal force, which activates the second, or subsequent, shredding element and produces blocks of a smaller dimension to facilitate, e.g., the carrying out of enzymatic reactions and subsequent recovery of reaction products.

For applications to extract components from polyacrylamide gels, the slot dimensions preferably range from 1 µm to 1 mm as a function of the force applied. For applications to extract components from agarose gels, the slot dimensions can be slightly larger, ranging from 1 µm to 3 mm as a function of the force applied.

Device manufacturing is preferably accomplished by injection molding. Preferred materials include polypropylene, PTFE (polytetrafluoroethylene, e.g., Teflon®), polyethylene, polycarbonate, polysulphone, ABS (acrylonitrile-butadiene-styrene copolymer) or an equivalent thermoplastic polymer. Existing molds currently used for production of certain centrifugal devices can be modified for the manufacture of a shredding device according to the invention by machining or by insertion of additional parts to form the slots, holes or openings of other shapes. Alternatively, a new mold is prepared to form the optimized geometry of the device bottom so as to achieve better sensitivity of the device performance as a function of centrifugal force. For example, the device is designed in such a way that a centrifugal force applied to the device controls the extent of opening between the shredding blades on the bottom of the device, causing a gel matrix to be shredded to fragments of a pre-defined size. Optimization of the device performance at the practical centrifugal force achievable in commercially available centrifuges can be achieved by altering the thickness of the cutting blade material. For example, a thicker weight (a "bulge") at the bottom of the cutting blade sector would allow the sector to swing outward at the lower centrifugal force. A shredding device can be optimized for use in an angled centrifuge rotor. At least three cutting blades are needed to ensure that the orientation of the slots in the rotor has a effect on the shredding performance In a multi-stage shredding device, the slots and blade size are optimized to achieve, first, crude shredding of gel pieces into cubes about 1 mm$^3$ for efficient washing and destaining in the top device, followed by a fine shredding into small fragments of 100-200 micrometers in size for enzymatic treatment and peptide extraction in the lower device. A similar device optimization process is carried out for the processing of agarose gels. For processing of these gels, the cutting slot opening has to be bigger than for acrylamide gels.

Shredding devices according to the invention can be optimized for use with positive pressure of air or other gas. The top of the device is sealed and connected to a source of pressurized air (gas). Positive pressure is then used to drive the gel fragment through the shredding blades. This form of pressure application is particularly suitable for the multi-well device configuration when multiple samples are processed simultaneously. Furthermore, this configuration is suitable for robotic implementation; i.e., sample loading and retrieval can be accomplished using standard liquid handling robotic manipulators. In a related embodiment, Shredding devices according to the invention can be optimized for use with a vacuum. The bottom of the shredding device is sealed against the vacuum manifold, which, in turn, contains the sample receiving tube. The vacuum is used to pull the sample through the shearing blades. Again, this configuration is considered suitable for robotic implementation; i.e., sample loading and retrieval can be accomplished using standard liquid handling robotic manipulators.

The performance of the device has been compared to a conventional in-gel digestion protocol using several gel-separated model proteins and complex proteomic samples, followed by relative quantification by either MALDI-TOF/TOF or nanoLC-Electrospray-IT-FTICR tandem mass spectrometry. A notable improvement in peptide recovery has been obtained for many proteins by using the device according to the invention as compared to the traditional in-gel digestion protocol. Application of the method of the invention is particularly useful for recoveries of high molecular weight hydrophobic peptides, presumably due to their higher affinity to the polyacrylamide gel lattice.

Referring to FIGS. 1-3, in one embodiment, the device according to the invention consists of a shredding insert 10 for a standard disposable, e.g., Eppendorf®, microcentrifuge tube 12, the insert having a small, deformable opening 14 at the end thereof. As shown further in FIGS. 5a-5c, opening 14 may be in the form of a series of slots, 16 in its bottom. For example, the slots forming the opening may be joined to form an X pattern.

Figure 4:
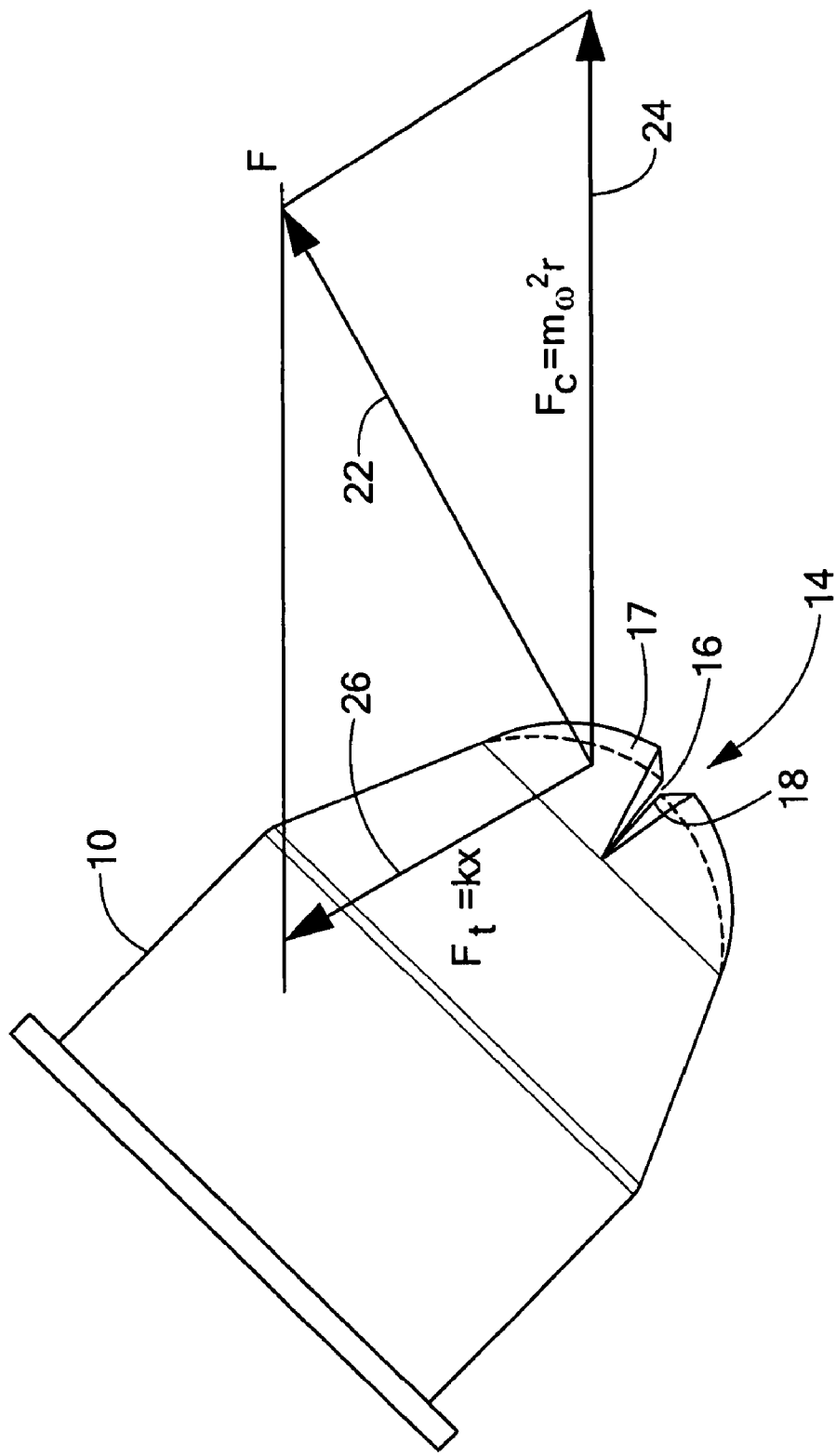
FIG. 4 is a free body diagram showing the forces on the device of FIG. 1, when subjected to a centrifugal force.

The size and configuration of the slots 16 the opening 14 are constructed during the manufacture of the insert and are designed in such a way that the dimensions and shape of the opening can be controlled during operation by a force, such as a centrifugal force, that pulls the individual sectors of the device bottom apart. In operation, a variable shearing force is provided on the gel pieces in the device insert as a function of, e.g., a centrifugal force applied to the shredding device. Referring to FIG. 4, the resulting force F 22, a vector sum of the centrifugal force $F_c$ 24 applied to the device at the angled centrifuge rotor, and the tensile force $F_t$ 26 of the device material, causes the quarter sector 17 of the device bottom to swing outward, opening the shredding slot 16 in the device bottom. The dimensions of the shredding slot opening will be proportional to the centrifugal force applied, assuming that the material properties and temperature remain constant. As the opening becomes sufficient for a portion of the gel material to be extruded through the shredding slot 16, that portion becomes sufficiently large to be cut away with the shredding blade 18 by the centrifugal force $F_c$ 24.

Figure 6A:
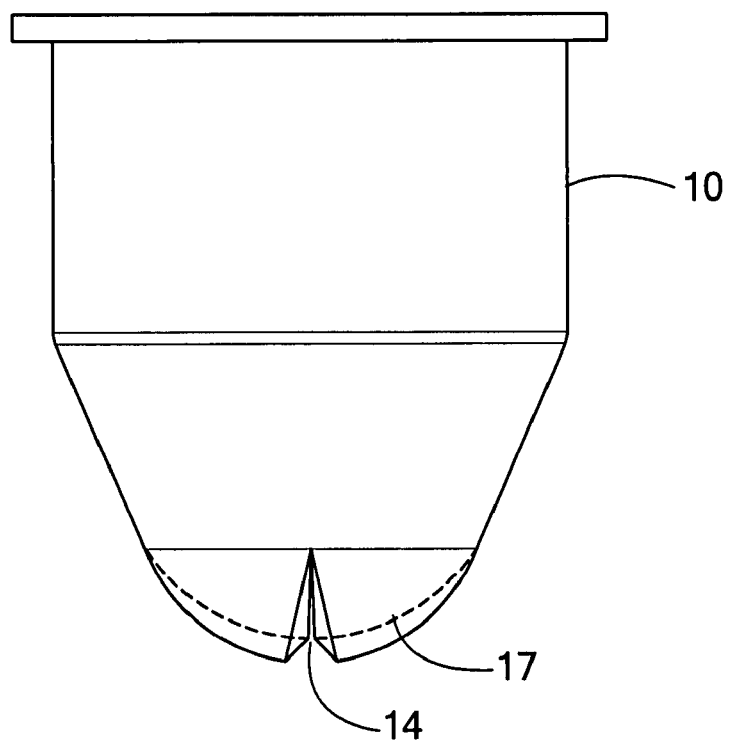
FIGS. 6a and 6b, and 7a and 7b show side and bottom views, respectively, of the embodiment of FIGS. 5a and 5b, under increasing centrifugal force.
Figure 6B:
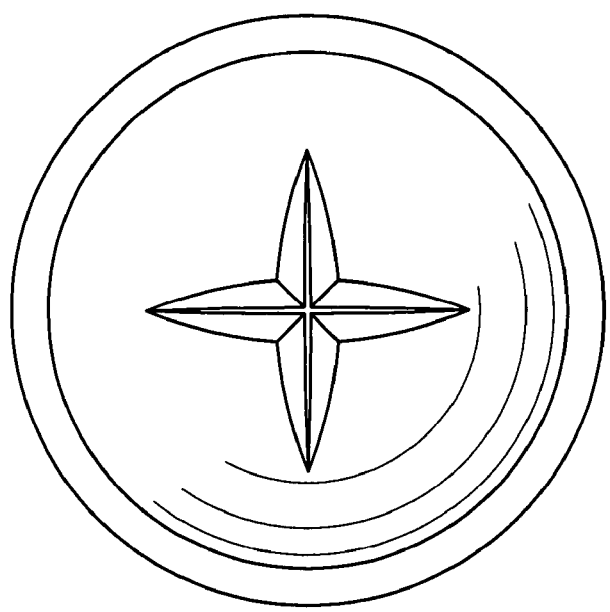
Figure 7A:
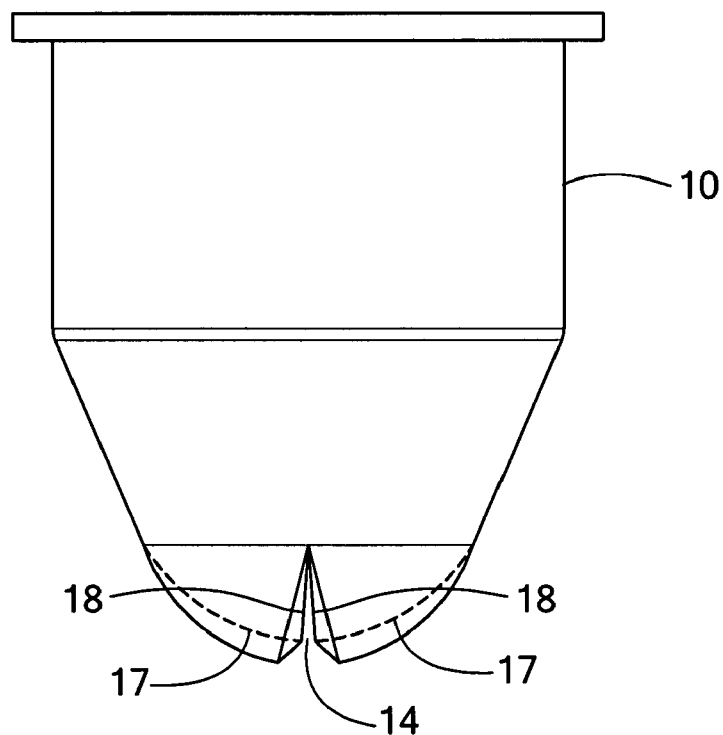
Figure 7B:
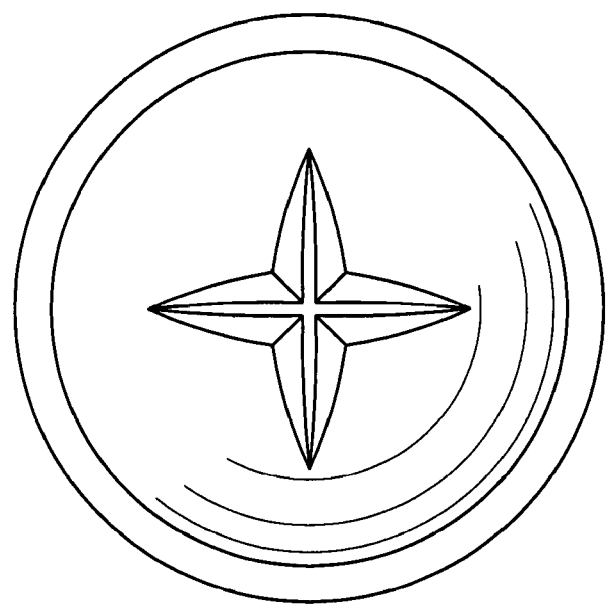
Figure 8:
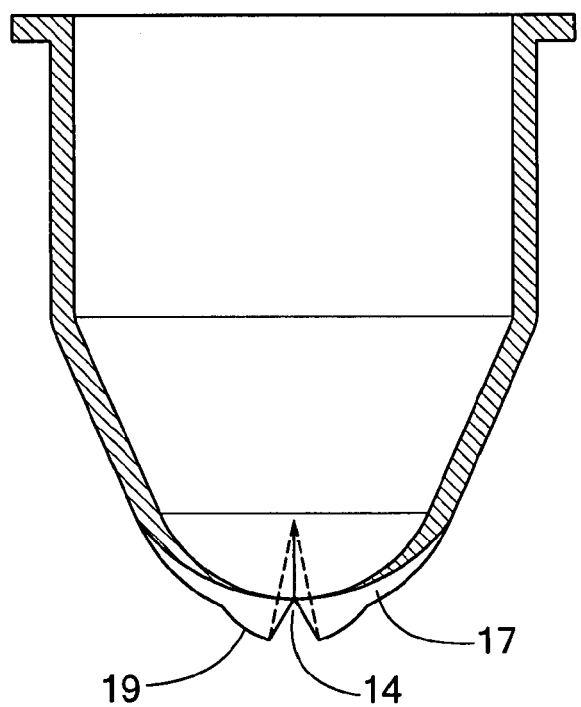

FIGS. 5a and 5b, 6a and 6b, and 7a and 7b show side and outside bottom schematic views, respectively, of another (more blunt) embodiment of a shredding device according to the invention with progressively more open shredding blades. (FIG. 5c is an inside bottom view of the device of FIG. 5a.) In FIGS. 5a and 5b, there is no force other than gravity on the inside bottom of the device and the shredding sectors 17, and the sectors remain closed. FIGS. 6a and 6b show the results of applying a small force to the bottom of the device. In this view, the sectors 17 have opened only enough for, e.g., a washing liquid to pass through. By FIGS. 7a and 7b, the increased force has opened the sectors sufficiently to serve as shredding blades 18. The embodiment of FIG. 8 shows how extra mass 19 may be added to the tips of the sectors 17 in a specific configuration so as to increase the movement of those sectors under the applied force. It is useful to note that while a single slot 16 may work exactly the same way, it would be important to orient the device in the typical angled rotor such that the slot is positioned horizontally, i.e., parallel the rotation plane. Multiple radial slots, such as 3, 4 or more, are necessary to guarantee that the device performance will be independent of the device orientation in the angled rotor. If centrifuges of the swinging bucket rotor type are employed, this consideration is not relevant, as the centrifugal force will act on all sector blades exactly the same way.

In another embodiment, as shown in FIG. 9a (exploded view) and 9b (nested view), a filter insert 30 is positioned between the shredding portion 10 and the receiving tube 12. The filter inserts are suggested when shredded material needs to be collected in its entirety or when necessary to prevent a contamination of the liquid eluted from the shredded material with small particles of the shredded material. Such filter inserts of appropriate dimensions are commercially available from several vendors, (e.g., Ultrafree-MC from the Millipore Corporation).

Figure 10A:
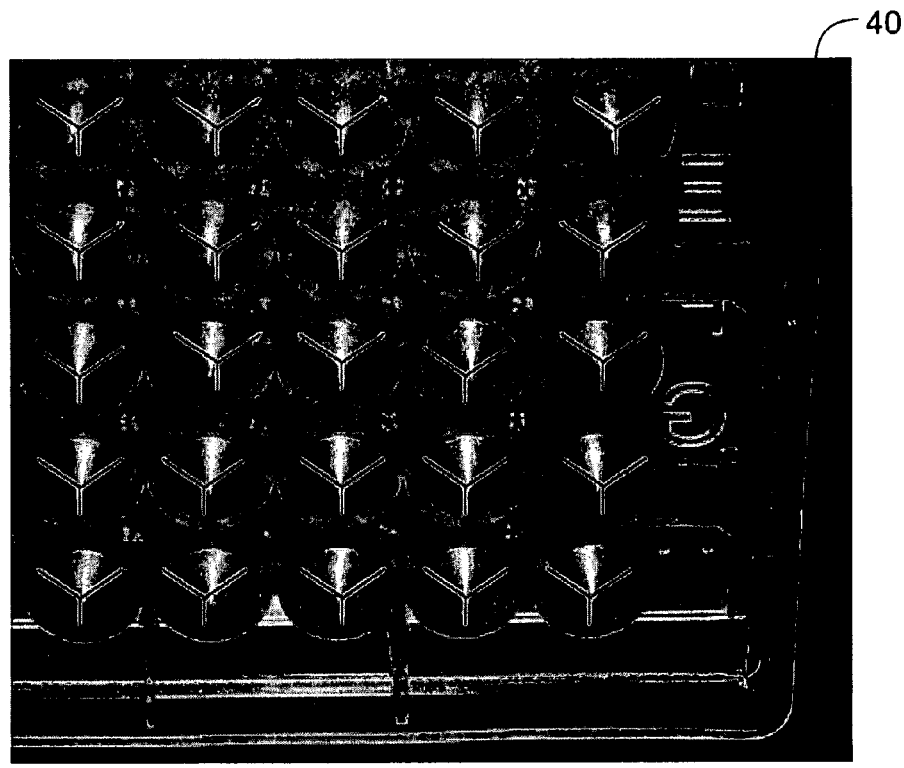
Figure 10B:
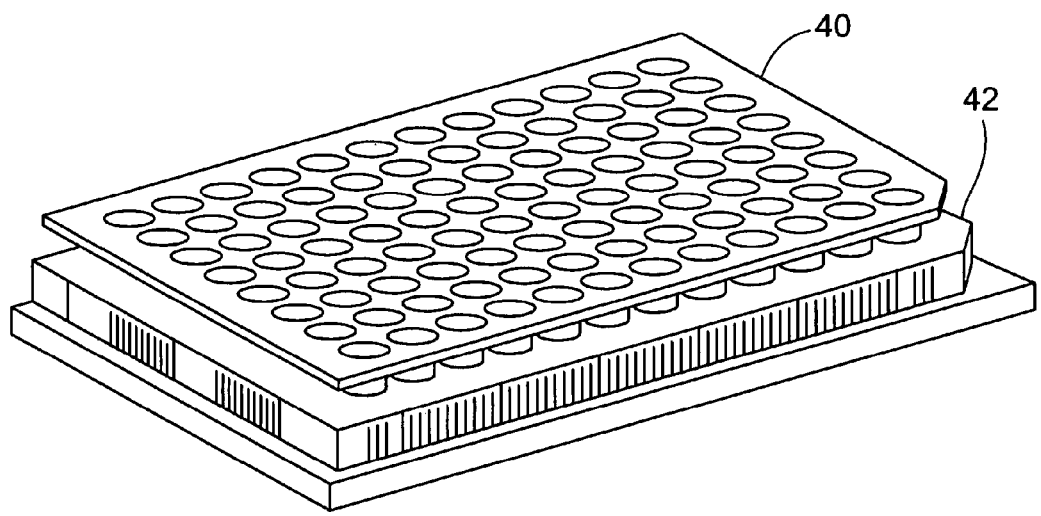

In yet another embodiment, as shown in FIG. 10a, a multiplicity of shredding devices can be arranged into a multi-well plate format 40. Such devices can contain, e.g., 12, 24, 48, 96, or 384 shredding elements to conform to the standardized robotic-friendly SBS (Society for Biomolecular Screening) microplate format. FIG. 10b shows a 96-well plate shredding device 40 with a collection plate 42. Multi-well devices can be used in conjunction with centrifugal force employing standard microplate centrifuge rotors. Alternatively, sample material can be passed through such devices by applying a vacuum, for example, in a standard manner to the sealed chamber underneath the device. In order to collect the shredded material, the sealed chamber contains a receiving plate of corresponding format aligned directly under the shredding plate.

Figure 12A:
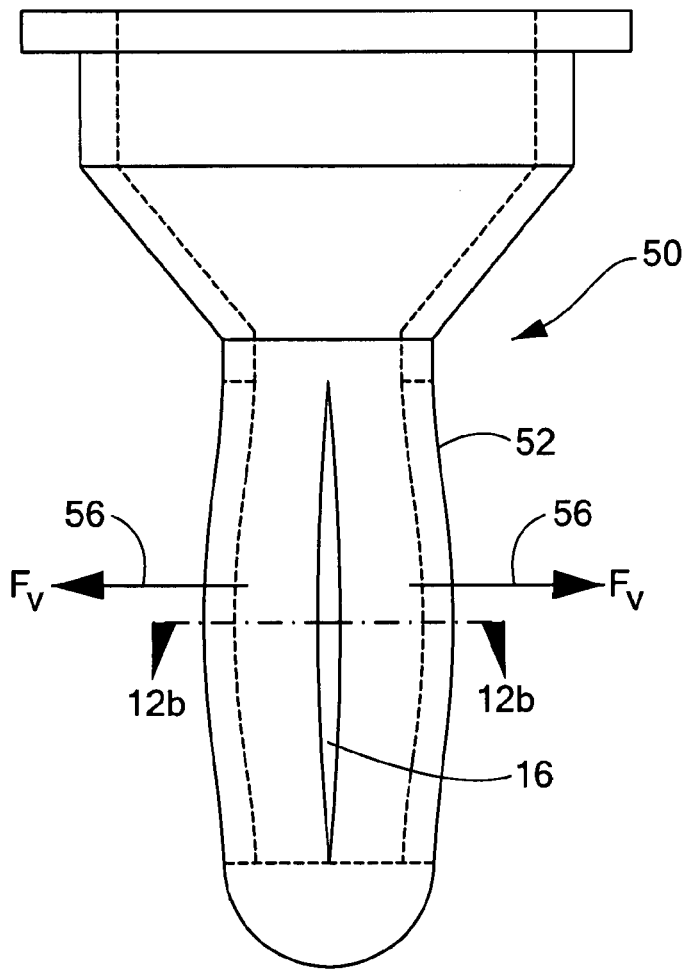
Figure 12B:
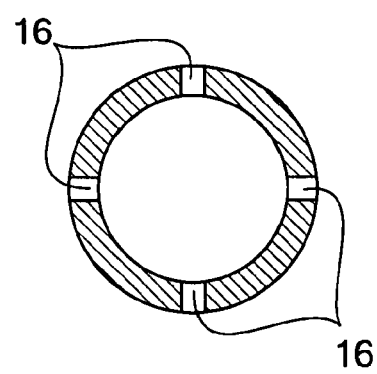

In another embodiment, as shown in FIGS. 11a, 11b, 12a and 12b, a combination of centrifugal force and vacuum is employed to assure that gel material is directed through the shearing slots with required force. Referring first to FIG. 11a, in this embodiment, the shredding device 50 has a funnel shape, where the gel plug can first be wedged into the narrow bottleneck portion 52 of the device by centrifugal force $F_c$ 54, followed by the subsequent application of vacuum Fv 56, as shown in FIG. 12a, to open the slots 16 on the sides of bottleneck portion 52 and pull the gel through.

A multi-stage shredding device 60, in which single device comprises two or more shredding elements, is shown in FIGS. 13 and 14. The second shredding element 64 is positioned directly below the first element 62, and an additional shredding element could be positioned below the second one. In the embodiment of FIG. 13, the openings of the individual shredding elements are configured in the same way; however, each subsequent shredding element is constructed from a less flexible material than the previous one. In the embodiment of FIG. 14, the opening of the first element 62 is slightly open compared to the opening of the second element 64. Such a configurations allow shredding of the sample material (gel) first to medium-size blocks at a medium centrifugal force, e.g., to facilitate more complete washing and removal of dyes and detergents. Subsequently, the medium-size gel blocks are processed at the higher centrifugal force, which activates the second, or subsequent, shredding element and produces blocks of a smaller dimension.

In use, the shredding device according to the invention allows washing and destaining of, e.g., gel plugs in situ prior to gel disintegration using a centrifugal force. The device is designed in such a way that the gel band or plug to be processed remains in the device while it is spun at a low centrifugal force, enabling exchange of solvents by centrifugation during wash and destain steps. Surface tension keeps solvents and buffers (up to 80% acetonitrile) in the device until the low centrifugal force is applied, which purges the solvent through the narrow deformable opening in the device into a receiving container. Fully destained gel plugs are shredded into slurry by means of the shredding blades as the gel pieces are forced through the shredding opening upon application of a high centrifugal force. Importantly, unlike the irregular gel slurry produced by manual methods, the fragments generated by use of the device according to the invention do not interfere significantly with the use of ZipTips® or robotic liquid handlers due to their uniform size distribution. It has been also found that shredded gel fragments tend to aggregate during acetonitrile extraction, which allows simplifying aspiration of the solution out of the test tube using a conventional gel loading tip.

The benefits of uniform gel "shredding" following the conventional wash and destain protocols have been illustrated in a preliminary experiment, where the gel plugs were "mashed" manually against the sample tube walls using a pipette tip. Reports of using a razor blade to slice the gel bands into blocks of 0.5-1 mm in size have been noted in the literature (Ong et al., 2005); however, such a process cannot be suggested for laboratories using a high-throughput proteomic workflow. In contrast, using the shredding device according to the invention, multiple samples can be simultaneously processed using a single laboratory centrifuge, which is compatible with the typical workflow in many proteomic laboratories.

In exemplary uses, a polyacrylamide gel can be shredded using the method of the invention to increase gel surface area and gel porosity, leading to improvements in protease enzyme access to its substrate proteins during the in-gel digestion experiment and to improvements in peptide product recovery after the digestion is complete. Shredding of agarose gel can be used to recover DNA or RNA, as in chromosomal DNA, plasmid DNA, mRNA, rRNA, etc. Shredded gel fragments can be captured on a membrane filter for subsequent washing, digestion and elution.

Shredding of a gel block into smaller fragments improves washing and destaining efficiency. Subsequently shred the resulting fragments into the slurry or into gel pieces of about 100 to 200 μm in diameter improves in-gel digestion and extraction of resulting peptides. Shredding of other materials such as polyvinyl alcohol gel samples or silicone gel samples for sample preparation improves extraction of various components from the gel sample. Examples include contact lens material for extraction of proteins, nucleic acids and other molecular entities; silicone implant material for extraction of any molecular entities which have penetrated into the polymer during its use in vivo; and preparation of cartilage samples for chemical or biochemical analysis, etc.

The following examples are presented to illustrate the advantages of the present invention and to assist one of ordinary skill in making and using the same. These examples are not intended in any way otherwise to limit the scope of the disclosure.

Materials and Methods
Protein Standards

Purified lyophilized protein standards were obtained from Sigma-Aldrich (St. Louis, Mo.). Stock solutions of equine heart myoglobin (MYO), bovine serum albumin (BSA) and chicken ovalbumin (OVA) were prepared in water at 33, 33 and 16 picomol per microliter, respectively, in a chaotropic sample solubilization solution, containing 7 M urea, 2 M thiourea, 2% CHAPS and 40 mM Tris-HCl. The resulting solutions were simultaneously reduced and alkylated by addition of 5 mM tributylphosphine (TBP) and 10 mM acrylamide and incubated at room temperature for 90 minutes. The resulting protein standard stock solution was kept at −20° C. prior to separation using SDS-PAGE.

The partially purified sample of human cannabinoid receptor CB-2 is available at NCBI Accession No. P34972.

Complex Proteomic Samples

For complex protein sample analysis, 100 mg aliquots of murine abdominal fat pad adipose tissue obtained from a wild type mouse were extracted using a Barocycler NEP3229 (Pressure BioSciences, West Bridgewater, Mass.) in 1.3 ml of 9 M urea, 4% CHAPS, using 30 cycles of hydrostatic pressure from ambient to 35,000 psi, where the high and ambient pressure were held for 20 seconds during each cycle. Subsequently, extracts were reduced and alkylated using 5 mM TBP and 10 mM acrylamide in the presence of 20 mM Tris for 90 minutes at room temperature, desalted and concentrated using 10 MWCO Amicon Ultra 4 ultrafiltration devices (Millipore, Billerica, Mass.) to the final volume of 50 μl.

Electrophoresis, Staining and Protein Spot Excision
Analysis of Protein Standards The protein standards were serially diluted to desired final concentrations with a 1D sample buffer (2% SDS, 20% glycerol, 0.01% BPB, 50 mM DTT, 62 mM Tris-HCl pH 6.8 with bromophenol blue added as a tracking dye) and loaded onto triplicate lanes of an SDS-PAGE system (NuPage 3-8% pre-cast gels, Invitrogen, Carlsbad, Calif.) at protein loads per lane ranging from 6.8 to 105 ng per lane. The gels were run under a constant current of 40 mA/gel. Electrophresis was stopped when the dye front was within 3 mm of the bottom of the gel.

Analysis of Mouse Adipose Tissue

Twenty microliter aliquots of a reduced and alkylated murine adipose tissue extract were separated on Criterion SDS-PAGE 8-16% gradient pre-cast gels (Bio-Rad Laboratories, Hercules, Calif.). Gels were fixed and stained with either SYPRO Ruby (Invitrogen, Carlsbad, Calif.) or ProteomIQ Blue (Proteome Systems, Woburn, Mass.) using protocols supplied by respective reagent vendors. Gel bands were excised from the gel using the GeneCatcher spot picking tips (The Gel Company, San Francisco, Calif.) or a sterile disposable scalpel. To ensure reproducibility of sample processing, each selected band was cut into identical pieces that were processed using either the gel shredder device according to the invention or a standard in-gel digestion procedure.

Washing, Destaining and Enzymatic Digestion

Gel plugs or lanes were washed once with 100 μL of 50 mM ammonium bicarbonate (ABC) and three times with 100 μL of 50% acetonitrile in 50 mM ABC. Gel pieces were dehydrated with 100 μL of 100% acetonitrile following each wash cycle. Following the last rehydration in ABC, every duplicate set of gel plugs was crushed gently into a slurry with the clean pipette tip or shredded using a device according to the invention. Washed and rehydrated control gel bands were cut into three blocks 1 mm×1 mm each using a clean surgical scalpel blade and placed into the standard 1 ml centrifuge tubes. Gel samples in both sets of tubes were dried in a SpeedVac centrifuge for 5 minutes. Twenty microliters of fresh trypsin solution (12.5 mg/mL) in 50 mM ABC buffer were added to each tube on ice, excess of enzyme solution having been discarded using the gel loading tips after 10 minutes of rehydration and replaced with an equivalent volume of fresh 25 mM ABC buffer, followed by an incubation for 12 hours at 36° C. Tubes were kept in a humidified chamber to prevent sample evaporation during incubation. Digestion was stopped by an addition of 10 μL of 1% TFA (in case of MALDI MS analysis) or 5% formic acid (in case of LC-MS/MS analysis) to each sample.

Peptide Extraction for MALDI-TOF/TOF (Matrix-Assisted Laser Desorption Ionization Time-Of-Flight Mass Spectrometry) Experiments Digest supernatants were aspirated with gel-loading tips and stored in a new set of tubes. Peptides remaining in the gel plugs or slurry were extracted with 50 μL of aqueous 50% acetonitrile containing 0.1% trifluoroacetic acid (TFA). Gel debris was centrifuged down. Extracted peptides were aspirated out and combined with the respective original digests. Gel plugs were shrunk by addition of 20 μL of 100% acetonitrile. After a centrifugal step, acetonitrile extracts were aspirated out and combined with the aqueous peptide solutions from the corresponding samples. The volume of the combined peptide extracts was reduced to approx. 5-10 μL in a SpeedVac centrifuge, followed by the addition of 10 μL of 0.2% TFA to compensate for possible loss of TFA in vacuum. Samples were purified by ZipTip μC18 and spotted onto a MALDI target for analysis. Internal standard peptides (angiotensin I and ACTH fragment 18-39) were added at the amount of 100 fmol each following tryptic digestion to allow relative quantification.

Peptide Extraction for LC-MS/MS Experiments

Extraction was carried out as outlined above, except 1% formic acid was used instead of TFA to stop digestion. Also, following the SpedVac volume reduction, samples were diluted in 0.1% aqueous formic acid to a final volume of about 20 μL and subjected to the HPLC separation.

Robotic Liquid Handling

Compatibility of the gel slurry with automated liquid handling robotic instrumentation has been tested using the Xcise proteomic robot (Shimadzu Scientific Instruments, Columbia, Md.). Washed, destained and dried aggregated gel slurry clusters produced by gel shredder devices according to the invention and whole control gel bands manually cut into four pieces were transferred to polypropylene 96-well microtiter plates (Granier, Nurtingen, Germany) and placed on the Xcise platform. The steps of dispensing of trypsin solution into wells, incubation of sealed microtiter plates, peptide extraction, ZipTip clean-up and spotting onto a MALDI-TOF target plate were programmed into the Xcise robot and were performed in an unattended fashion. No plugging of ZipTips was observed when a gel slurry was used. Adequate sample spots were produced, resulting in good MALDI-TOF/TOF spectra being obtained, as described below.

MALDI-TOF/TOF Mass Spectrometry

Samples were analyzed on an ABI 4700 MALDI-TOF (Applied Biosystems, Foster City, Calif.) mass spectrometer in reflectron and tandem mass spectrometry (MS/MS) modes using α-cyano hydroxycinnamic acid (CHCA) as the matrix (7 mg/mL in 50% ACN:water, 0.1% TFA solution). Calibration was performed using a panel of three external standard peptides positioned close to every sample spots. Relative quantification has been performed by averaging the ratios of isotope cluster areas, determined using Data Explorer version 4.6 (Applied Biosystems) for each of the several selected tryptic peptides to the average isotope cluster area of exogenous internal standard peptides. Assessment of proteolytic cleavage efficiency was carried out by monitoring the number of peptides resulting from missed tryptic cleavages detected in the samples digested under various conditions.

Nanoflow LC-MS/MS

The LC-MS system used for peptide analysis from in-gel digests was an Ultimate 3000 nanoflow LC pump (Dionex, Mountain View, Calif.) coupled to an LTQ-FTMS instrument (Thermo Electron, San Jose, Calif.) equipped with a PicoView ESI sources (New Objective, Woburn, Mass.). The in-gel digested peptides were loaded and separated using a self-packed reversed phase column (10 cm, 75 μm i.d., Magic C18, 3 μm particle size, 200 Å pore size). The flow rate was set at 200 mL/min for both sample loading and separation. A shallow gradient elution, using 0.1% (v/v) formic acid in water (mobile phase A) and 0.1% (v/v) formic acid in acetonitrile (mobile phase B), was performed by starting at 2% mobile phase B and increasing to 40% mobile phase B over 65 min, and then to 90% mobile phase B over 15 min, and finally constant 90% mobile phase B for 10 min. Before the next sample was injected, the C-18 column was equilibrated at 2% mobile phase B for 30 min. Before loading, samples were diluted by mobile phase A and clarified by centrifugation at 10,000×g for 5 min to protect the column from clogging. Moreover, blank runs were employed to minimize the carryover between injections of different samples.

The mass spectrometer was operated in the data-dependent mode, switching automatically between MS and $MS^2$. Briefly, the survey full-scan MS spectra with 1 microscan (m/z 400-2000) were acquired in an FT-ICR cell with mass resolution of 100,000 at m/z 400 (with target ion counts at $2\times10^6$ ions), and then the top 9 most abundant ions were isolated as precursor ions for sequential data-dependent $MS^2$ scans. For the data-dependant mode, dynamic exclusion was utilized with 2 repeat counts, repeat duration of 30 s, exclusion list 200, and exclusion duration of 30 s. The normalized collision energy was 28% for all $MS^2$ scans.

Peptide Identification Via Database Searching

MS spectra collected using the AB4700 instrument were searched against a UniProt database using a publicly available Mascot server. The number of unidentified peaks was recorded as a measure of sample purity, the presence of peaks potentially originating from polyacrylamide breakdown and other sources.

LC-MS files were processed using CPAS ver. 1.6 (KeyLab, Seattle, Wash.) using Sequest algorithm (ver. 27 rev. 13). The database search was performed against SwissProt database (release 52) consisting of normal and reverse sequences to allow estimation of the false positive rate. The following peptide filtering criteria were used to select correct identifications: PeptideProphet probability >0.95, XCorr values: 1.9 (1+); 2.2 (2+) and 3.7 (3+), estimated rate of false positive identifications: 1.5%.

Quantitative Analysis

For samples analyzed by AB4700, relative quantification was determined by averaging the ratios of isotope cluster areas for each of the several selected tryptic peptides to the average isotope cluster area of the exogenous internal standard peptides. Assessment of proteolytic cleavage efficiency was determined by monitoring the number of peptides resulting from missed tryptic cleavages detected in the samples digested under various conditions.

The effectiveness of a gel shredding device according to the invention vs. a standard in-gel digestion method, for samples where proteins were identified by LC-MS analyses, was estimated based on the number of proteins and peptides identified for respective samples.

In-Gel Digestion Performance and Peptide Recovery

Shredding devices according to the invention offer reproducible and automated in-gel digestion workflow. Relative quantification was used to determine the effect of device use on tryptic peptide recovery in both MALDI-TOF/TOF and LC-MS/MS experiments from the in-gel digests of gel bands, containing identical amount of protein.

Samples consisting of four standard proteins at different concentrations were separated using SDS-PAGE and processed using a prior art in-gel digestion protocol, in-solution digestion and the shredding method according to the invention. Relative quantification of the results using intensities of selected peptides shows a general trend of higher tryptic peptide recovery from the in-gel digests of gel bands, containing identical amount of protein standards, when gel is subjected to mechanical disintegration using the method of the invention. Compared to the conventional in-gel digestion, the new method improves peptide recoveries at least two-fold as compared to the conventional in-gel digestion method. It was also shown that the relative abundance of peptide ions resulting from protein digests produced in solution may still be considerably higher; however, this observation becomes less significant for analysis of membrane proteins such as human cannabinoid receptor CB-2, a member of the GPCR family. Peptide recovery from digests of this protein carried out using the instant invention approaches the recovery from solution digests of the same amount of this protein. Moreover, a generally higher number of peptides and higher peptide recovery is observed when this method is used with a wide variety of proteins from large SDS-PAGE gel sections. Early reports on quantitative assessment of peptide losses during the in-gel digestion process have revealed that most losses were related to peptide binding to the surface of polymer laboratory containers (Speicher et al., 2000). With the introduction of new low binding polypropylene and siliconized tubes the peptide losses to surfaces no longer appear to be a major issue. In standard protocols, most of the losses typically occur due to interference of the gel matrix with enzymatic digestion and extraction of resulting peptides. Controlled reduction of gel particle size allows acrylamide gel to swell more and facilitate better rehydration with enzymes as well as peptide extraction.

Proteomic Analysis of Mouse Adipose Tissue Using Gel-LC MS Strategy

In order to evaluate the performance of Gel Shredder for proteomic applications, protein extract from mouse adipose tissue was used as a model sample. The proteins were separated by SDS-PAGE and the resulting gel lanes cut into three sections corresponding to high, medium and low molecular weight regions. Each section was split into two pieces that were processed either using Gel Shredder or conventional in-gel digestion protocol. Extracted peptides were analyzed in duplicates by LC-MS using the LTQ-FT instrument.

Table I shows the combined number of unique protein identifications obtained for samples processed using the device according to the invention and a conventional in-gel digestion protocol. The total number of identified proteins is higher in the case of sample processing using the method of the invention, where 89 additional proteins were identified compared to additional 55 proteins identified using conventional in-gel digestion protocol. It is interesting to compare the number of additional proteins identified in different MW sections. For the high MW section, the number of additional proteins almost doubled, suggesting significantly improved recoveries for higher molecular weight proteins. On the other hand, a similar number of additional proteins were identified in the low MW section, i.e., 21 compared to 17 using conventional in-gel digestion procedure. In addition, Table 1 shows the number of unique peptides that for proteins identified using both protocols. Out of total 251 proteins that were identified using both protocols, 95 proteins were identified by greater number of unique peptides using Gel Shredder compared to 40 proteins using conventional protocol. Similar to the case of additional proteins, the highest gain can be seen for high MW fraction where out of 93 protein identified by both protocols, processing using Gel Shredder resulted in 44 proteins with more unique peptides compared to 15 in the case of conventional in-gel digestion. For the low MW section, the trend reversed.

TABLE 1

Summary of protein identifications in Gel-LC MS/MS experiments

| Groups | Total IDs | High MW | Mid MW | Low MW |
|---|---|---|---|---|
| Proteins identified by protocol A | 89 | 42 | 55 | 17 |
| Proteins identified by protocol B | 55 | 25 | 39 | 21 |
| Proteins identified by protocol A and B | 251 | 93 | 167 | 48 |
| Unique peptides: A > B | 95 | 44 | 59 | 7 |
| Unique peptides: A = B | 116 | 34 | 76 | 26 |
| Unique peptides: A < B | 40 | 15 | 32 | 15 |

Protocol A: method according to the invention; Protocol B: standard in-gel digestion procedure.
Note:
Peptide filtering criteria: PeptideProphet >0.95, XCorr values: 1.9 (1+); 2.2 (2+) and 3.7 (3+). Estimated rate of false positive peptide identifications: 1.5%

Improvements in peptide recovery are believed to be attributable to several facts: 1) smaller gel pieces can easily absorb more solution of trypsin leading to better digestion efficiency and 2) after the in-gel digestion, the resulting peptides can be extracted with higher recoveries, particularly for more hydrophobic peptides. On the other hand, smaller gel pieces may potential lead to lower recoveries for small proteins as shown for low molecular weight fraction of SDS-PAGE gel.

Besides providing improved peptide recoveries, the method of the invention also automates and simplifies, thus minimizing sample losses in several steps in the in-gel digestion protocol. First, the selected gel band does not need to be cut into small cubes manually, which is especially advantageous for processing of gel sections, such as in gel-LC type of proteomic experiments. Second, processing samples in parallel using a laboratory centrifuge removes a significant amount of time necessary for pipetting of solutions. Third, the processing is done in one closed container, which prevents losses during sample handling. In addition, compared to expensive robotic instrumentation available for in-gel digestion, use of the device according to the invention requires only a laboratory centrifuge and provides a throughput compatible with the requirements of a typical proteomic laboratory.

REFERENCES

Bergen H R 3rd, Muddiman D C, O'Brien J F and Hoyer J D. Normalization of relative peptide ratios derived from in-gel digests: applications to protein variant analysis at the peptide level. *Rapid Commun Mass Spectrom.* 2005, 19: 2871-2877.

Bunai K, Nozaki M, Hamano M, Ogane S, Inoue T, Nemoto T, Nakarishi H and Yamane K. Proteomic analysis of acrylamide gel separated proteins immobilized on polyvinylidene difluoride membranes following proteolytic digestion in the presence of 80% acetonitrile. *Proteomics.* 2003, 3: 1738-1749.

Castellanos-Serra L, Ramos Y and Huerta V. An in-gel digestion procedure that facilitates the identification of highly hydrophobic proteins by electrospray ionization-mass spectrometry analysis. *Proteomics.* 2005, 5: 2729-2738.

de Godoy L M F, Olsen J V, de Souza G A, Li G, Mortensen P and Mann M. Status of complete proteome analysis by mass spectrometry: SILAC labeled yeast as a model system. *Genome Biology.* 2006, 76: R50.

Finehout E J and Lee K H. Comparison of automated in-gel digest methods for femtomole level samples. *Electrophoresis.* 2003, 24: 3508-3516.

Havliš J et al. Fast-response proteomics by accelerated digestion of proteins. *Anal. Chem.* 2003, 75: 1300-1306.

Havliš J and Schevchenko A. Absolute quantification of proteins in solutions and in polyacrylamide gels by mass spectrometry. *Anal Chem.* 2004, 76: 3029-3036.

Katayama H, Satoh K, Takeuchi M, Deguchi-Tawarada M, Oda Y and Nagasu T. Optimization of in-gel protein digestion system in combination with thin-gel separation and negative staining in 96-well plate format. *Rapid Commun Mass Spectrom.* 2003, 17: 1071-1078.

Katayama H, Tabata T, Ishihama Y, Sato T, Oda Y and Nagasu T. Efficient in-gel digestion procedure using 5-cyclohexyl-1-pentyl-beta-D-maltoside as an additive for gel-based membrane proteomics. *Rapid Commun Mass Spectrom.* 2004, 18: 2388-2394.

Kumarathasan P, Mohottalage S, Goegan P and Vincent R. An optimized protein in-gel digest method for reliable proteome characterization by MALDI-TOF-MS analysis. *Anal Biochem.* 2005, 346: 85-89. Epub 2005, Jun. 21.

Lopez-Ferrer D, Capelo J L and Vazquez J. Ultra fast trypsin digestion of proteins by high intensity focused ultrasound. *J Proteome Res.* 2005, 4: 1569-1574.

Lu X and Zhu H. Tube-gel digestion: a novel proteomic approach for high throughput analysis of membrane proteins. *Mol Cell Proteomics.* 2005, 4: 1948-1958.

Nomura E, Katsuta K, Ueda T, Toriyama M, Mori T and Inagaki N. Acid-labile surfactant improves in-sodium dodecyl sulfate polyacrylamide gel protein digestion for matrix-assisted laser desorption/ionization mass spectrometric peptide mapping. *J Mass Spectrom.* 2004, 39: 202-207.

Ong, S E, Mortensen P, and Mann M. Poster A050496, *Proceedings of the 53rd ASMS Conference on Mass Spectrometry*, San Antonio, Tex., 2005.

Russell W K, Park Z Y and Russell D H. Proteolysis in mixed organic-aqueous solvent systems: applications for peptide mass mapping using mass spectrometry. *Anal. Chem.* 2001, 73:2682-2685.

Speicher K D et al. Systematic analysis of peptide recoveries from In-Gel digestions for protein identifications in proteome studies. *Journal of Biomolecular Techniques.* 2600, 11: 74-86.

Strader M B et al. Efficient and specific trypsin digestion of microgram to nanogram quantities of proteins in organic-aqueous solvent systems. *Anal. Chem.* 2006, 78: 125-134.

Sun W, Gao S, Wang L, Chen Y, Wu S, Wang X, Zheng D and Gao Y. Microwave-assisted protein preparation and enzymatic digestion in proteomics. *Mol Cell Proteomics.* 2006, 5:769-776.

Terry D E, Umstot E and Desiderio D M. Optimized sample-processing time and peptide recovery for the mass spectrometric analysis of protein digests. *J Am Soc Mass Spectrom.* 2004, 15: 784-794.

Vasilescu J. Zweitzig D R, et al. The proteomic reactor facilitates the analysis of affinity-purified proteins by mass spectrometry: application for identifying ubiquitinated proteins in human cells. *J Proteome Res.* 2007, 6: 298-305.

Yokono T, Mineki R, Taka H. Kotaniguchi H and Murayama K. Improvement of automatic in-gel digestion by in situ alkylation of proteins. *J Biomol Tech.* 2003, 14: 191-196.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A device for washing and/or shredding a material under an applied external force, said device comprising:
 a substantially cylindrical device body extending from an upper end to a lower end, the cylindrical portions of said device body defining a longitudinal axis from the upper end to the lower end, the device body having an inner surface and an outer surface;
 a fixed opening at the upper end of the device body;
 a mounting fitting on the cylindrical portion of said device body adjacent the upper end for mounting the device body coaxially within a centrifuge tube; and
 a deformable opening area in said device body, wherein said deformable opening area is formed of a deformable material and is disposed at the lower end of said device body, wherein the deformable opening area has a thickness extending between an inner surface and an outer surface of said device body, the inner surface of the deformable opening area being contiguous with the inner surface of the device body, and the outer surface of the deformable opening area being contiguous with the outer surface of the device body, wherein said deformable opening area has an opening deformable at least sufficiently for the passage of liquid under an externally applied force greater than ambient pressure, said force comprising centrifugal force or positive or negative pressure from a gas or liquid, and wherein said deformable opening area opening remains closed to the passage of liquid under ambient pressure.

2. The device of claim 1, wherein said opening in said deformable opening area comprises three or more slots formed therein, said slots meeting at and extending radially from a common point, and wherein:
 each slot comprises two walls each extending through the thickness of the deformable opening area;
 the walls of each slot are disposed at an angle to each other such that the walls are closest to each other at the inner surface of the deformable opening area and are farthest from each other at the outer surface of the deformable opening area;
 the walls of each slot intersect the inner surface of the deformable opening area to form a cutting edge; and
 the walls of each slot are deformable to widen at the inner surface of the deformable opening area.

3. The device of claim 2, wherein the opening in said deformable opening area comprises four slots.

4. The device of claim 1, wherein the opening in said deformable opening area comprises a spiral slot formed therein, said spiral decreasing from the outer region of said deformable opening area to the center region of said deformable opening area.

5. The device of claim 1, wherein said deformable opening area comprises an elastomeric material.

6. The device of claim 1, wherein said deformable opening area comprises a polymer.

7. The device of claim 1, wherein said deformable opening area comprises a thermoplastic polymer.

8. The device of claim 1, wherein the deformable opening area comprises polypropylene, polytetrafluoroethylene, polyethylene, polycarbonate, polysulphone or ABS.

9. The device of claim 1, wherein said mounting fitting comprises an annular shoulder at the upper end of said device body extending radially outwardly with respect to the longitudinal axis of said device body.

10. A system for washing and/or shredding a material under an applied external force, said system comprising:
 a device comprising a substantially cylindrical device body extending from an upper end to a lower end, the cylindrical portions of said device body defining a longitudinal axis from the upper end to the lower end, the device body having an inner surface and an outer surface; a fixed opening at the upper end of the device body; a mounting fitting on the cylindrical portion of said device body adjacent the upper end for mounting the device body coaxially within a centrifuge tube; and a deformable opening area in said device body, wherein said deformable opening area is formed of a deformable material and is disposed at the lower end of said device body, wherein the deformable opening area has a thickness extending between an inner surface and an outer surface of said device body, the inner surface of the deformable opening area being contiguous with the inner surface of the device body, and the outer surface of the deformable opening area being contiguous with the outer surface of the device body, wherein said deformable opening area has an opening deformable at least sufficiently for the passage of liquid under an externally applied force greater than ambient pressure, said force comprising centrifugal force or positive or negative pressure from a gas or liquid, and wherein said deformable opening area opening remains closed to the passage of liquid under ambient pressure; and a collection device, wherein said collection device has a substantially cylindrical body having an open top and a closed bottom and wherein said device is sized to fit snugly into said collection device, through the open top thereof.

11. The system of claim 10, comprising two or more of said device.

12. The system of claim 11, wherein said devices are nested in series.

13. The system of claim 11 comprising two or more of said collection device wherein the collection devices are configured in parallel in a multi-well format.

14. The system of claim 13, wherein said devices are configured in parallel in a multi-well format in alignment with said collection devices.

15. A method for washing and/or shredding a material under an applied external force, said method comprising the steps of:

providing a device comprising a substantially cylindrical device body extending from an upper end to a lower end, the cylindrical portions of said device body defining a longitudinal axis from the upper end to the lower end, the device body having an inner surface and an outer surface; a fixed opening at the upper end of the device body; a mounting fitting on the cylindrical portion of said device body adjacent the upper end for mounting the device body coaxially within a centrifuge tube; and a deformable opening area in said device body, wherein said deformable opening area is formed of a deformable material and is disposed at the lower end of said device body, wherein the deformable opening area has a thickness extending between an inner surface and an outer surface of said device body, the inner surface of the deformable opening area being contiguous with the inner surface of the device body, and the outer surface of the deformable opening area being contiguous with the outer surface of the device body, wherein said deformable opening area has an opening deformable at least sufficiently for the passage of liquid under an externally applied force greater than ambient pressure, said force comprising centrifugal force or positive or negative pressure from a gas or liquid, and wherein said deformable opening area opening remains closed to the passage of liquid under ambient pressure;

inserting into said body of said device a portion of gel from which a sample is to be recovered;

washing said gel portion with a washing liquid;

removing said washing liquid using a first externally applied force greater than ambient pressure, said first force comprising centrifugal force or positive or negative pressure from a gas or liquid; and shredding said gel using a second externally applied force greater than ambient pressure, said second force comprising centrifugal force or positive or negative pressure from a gas or liquid, wherein said second force is greater than said first force.

* * * * *